United States Patent
Tadano et al.

(10) Patent No.: US 10,702,182 B2
(45) Date of Patent: Jul. 7, 2020

(54) MYOELECTRIC SENSOR

(71) Applicants: NATIONAL UNIVERSITY CORPORATION HOKKAIDO UNIVERSITY, Hokkaido (JP); NIPRO CORPORATION, Osaka (JP); HARADA ELECTRONICS INDUSTRY CO., LTD., Hokkaido (JP)

(72) Inventors: Shigeru Tadano, Hokkaido (JP); Yoshihiko Sano, Osaka (JP); Masahide Harada, Hokkaido (JP)

(73) Assignees: NIPRO CORPORATION, Osaka (JP); HARADA ELECTRONICS INDUSTRY CO., LTD., Hokkaido (JP)

( * ) Notice: Subject to any disclaimer, the term of this patent is extended or adjusted under 35 U.S.C. 154(b) by 372 days.

(21) Appl. No.: 15/543,346

(22) PCT Filed: Jan. 12, 2016

(86) PCT No.: PCT/JP2016/050613
§ 371 (c)(1),
(2) Date: Jul. 13, 2017

(87) PCT Pub. No.: WO2016/117404
PCT Pub. Date: Jul. 28, 2016

(65) Prior Publication Data
US 2018/0000373 A1   Jan. 4, 2018

(30) Foreign Application Priority Data
Jan. 19, 2015  (JP) ................................ 2015-007661

(51) Int. Cl.
*A61B 5/0492*   (2006.01)
*G06F 3/01*    (2006.01)
*A61B 5/00*    (2006.01)

(52) U.S. Cl.
CPC .......... *A61B 5/0492* (2013.01); *A61B 5/6824* (2013.01); *A61B 5/6828* (2013.01);
(Continued)

(58) Field of Classification Search
CPC .................................................... A61B 5/1492
See application file for complete search history.

(56) References Cited

U.S. PATENT DOCUMENTS 9,600,030 B2 *  3/2017  Bailey .................... G06F 1/163
2009/0327171 A1  12/2009  Tan et al.
(Continued)

FOREIGN PATENT DOCUMENTS

CN   101879062 A   11/2010
CN   101919692 A   12/2010
(Continued)

OTHER PUBLICATIONS

Notice of Ground for Rejection issued by the Japanese Patent Office in relation to Japanese Application No. 2015-007661 dated Sep. 5, 2018 along with English translation (4 pages).
(Continued)

*Primary Examiner* — Lee S Cohen
(74) *Attorney, Agent, or Firm* — Robert P. Michal, Esq.; Carter, DeLuca & Farrell LLP

(57) ABSTRACT

A myoelectric sensor for detecting myoelectric signals which accompany body movement includes: a wearing band that is elastic, expandable, and circular, and that is worn around a limb to surround the limb tightly; myoelectric detection units a plurality of which are disposed in the circumferential direction on the wearing band with intervals therebetween so as to cause each of a plurality of myoelectric detection electrodes to be in close contact with the surface of the limb, and which detect myoelectric signals from corresponding positions on the limb using the myo-
(Continued)

electric detection electrodes; and connection cables that electrically connect mutually adjacent myoelectric detection units and thereby transmit the myoelectric signals. The connection cables each include a bent portion, the bent shape of which changes in response to changes in the distance between the mutually adjacent myoelectric detection units.

4 Claims, 3 Drawing Sheets

(52) U.S. Cl.
CPC ............ *A61B 5/6831* (2013.01); *G06F 3/015* (2013.01); *A61B 2562/046* (2013.01); *A61B 2562/164* (2013.01); *A61B 2562/166* (2013.01)

(56) References Cited

U.S. PATENT DOCUMENTS

| | | | | |
|---|---|---|---|---|
| 2014/0334083 | A1* | 11/2014 | Bailey | G06F 1/163 361/679.03 |
| 2015/0025355 | A1* | 1/2015 | Bailey | A61B 5/681 600/390 |
| 2015/0065840 | A1* | 3/2015 | Bailey | A61B 5/6802 600/384 |
| 2015/0234426 | A1 | 8/2015 | Bailey et al. | |
| 2015/0261307 | A1 | 9/2015 | Morikawa et al. | |

FOREIGN PATENT DOCUMENTS

| | | |
|---|---|---|
| CN | 103315737 A | 9/2013 |
| CN | 203234739 U | 10/2013 |
| CN | 103853333 A | 6/2014 |
| CN | 103948388 A | 7/2014 |
| JP | H07163607 A | 6/1995 |
| WO | 2014186370 A1 | 11/2014 |
| WO | WO-2014/208074 A1 | 12/2014 |
| WO | WO-2015123445 A1 | 8/2015 |

OTHER PUBLICATIONS

Extended Eurpoean Search Report issued by the European Patent Office in relation to European Application No. 16740011.8 dated Nov. 16, 2018 (7 pages).

Chinese Office Action issued by the State Intellecutal Property Office in relation to Chinese Application No. 201680004637.5 dated Jun. 28, 2019 along with English language translation (12 pages total).

Written Opinion of the International Searching Authority issued by the Japanese Patent Office acting as the International Searching Authority in relation to International Patent Application No. PCT/JP2016/050613 dated Mar. 15, 2016 (4 pages).

International Search Report issued by the Japanese Patent Office acting as the International Searching Authority in relation to International Patent Application No. PCT/JP2016/050613 dated Mar. 15, 2016 (3 pages) along with English language translation (1 page).

* cited by examiner

[FIG.1]
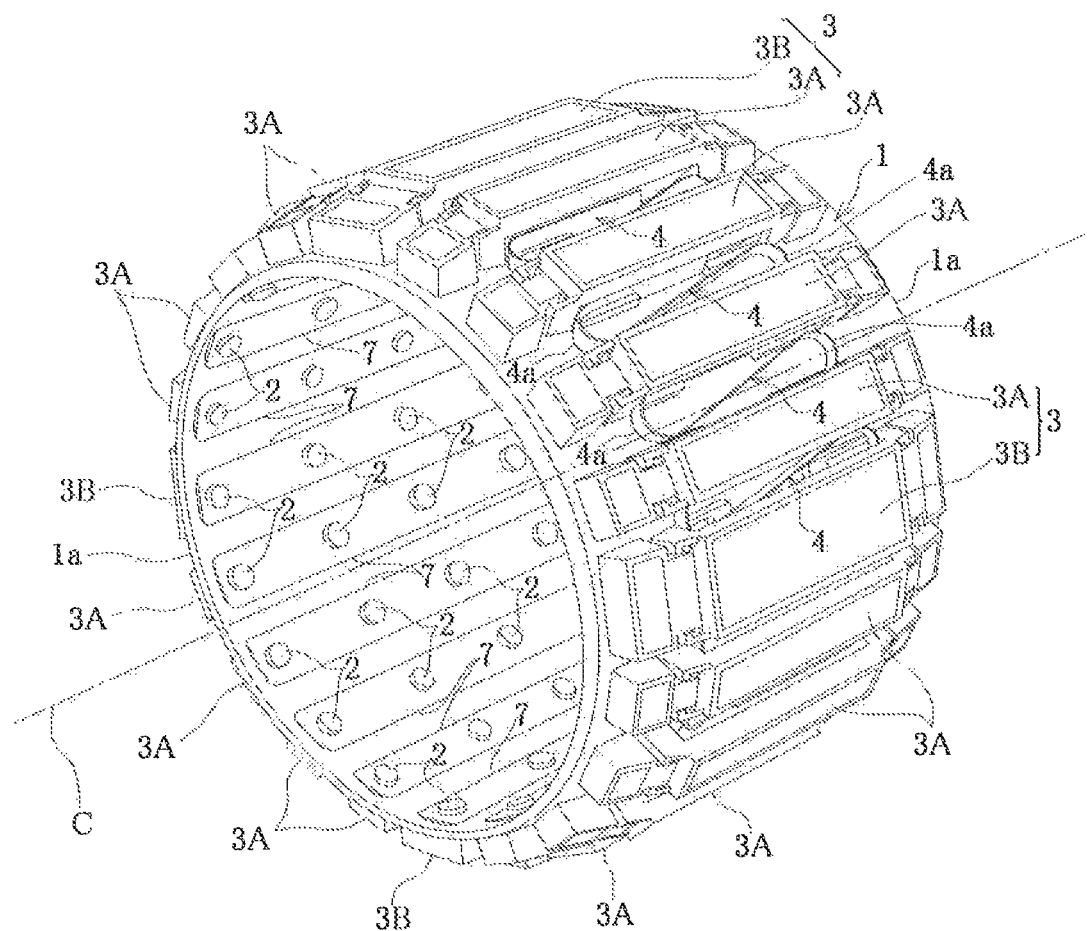

[FIG.2]
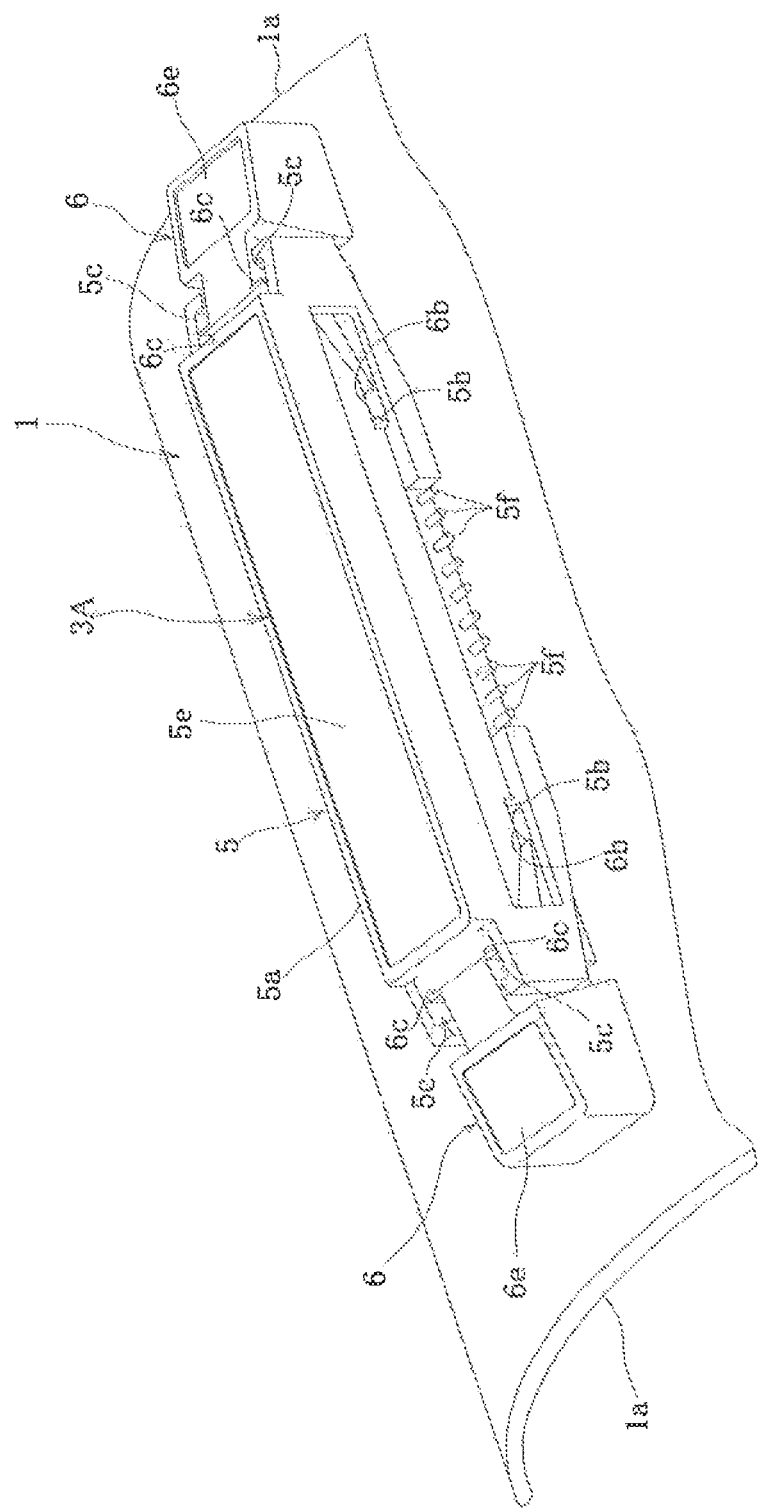

[FIG.3]
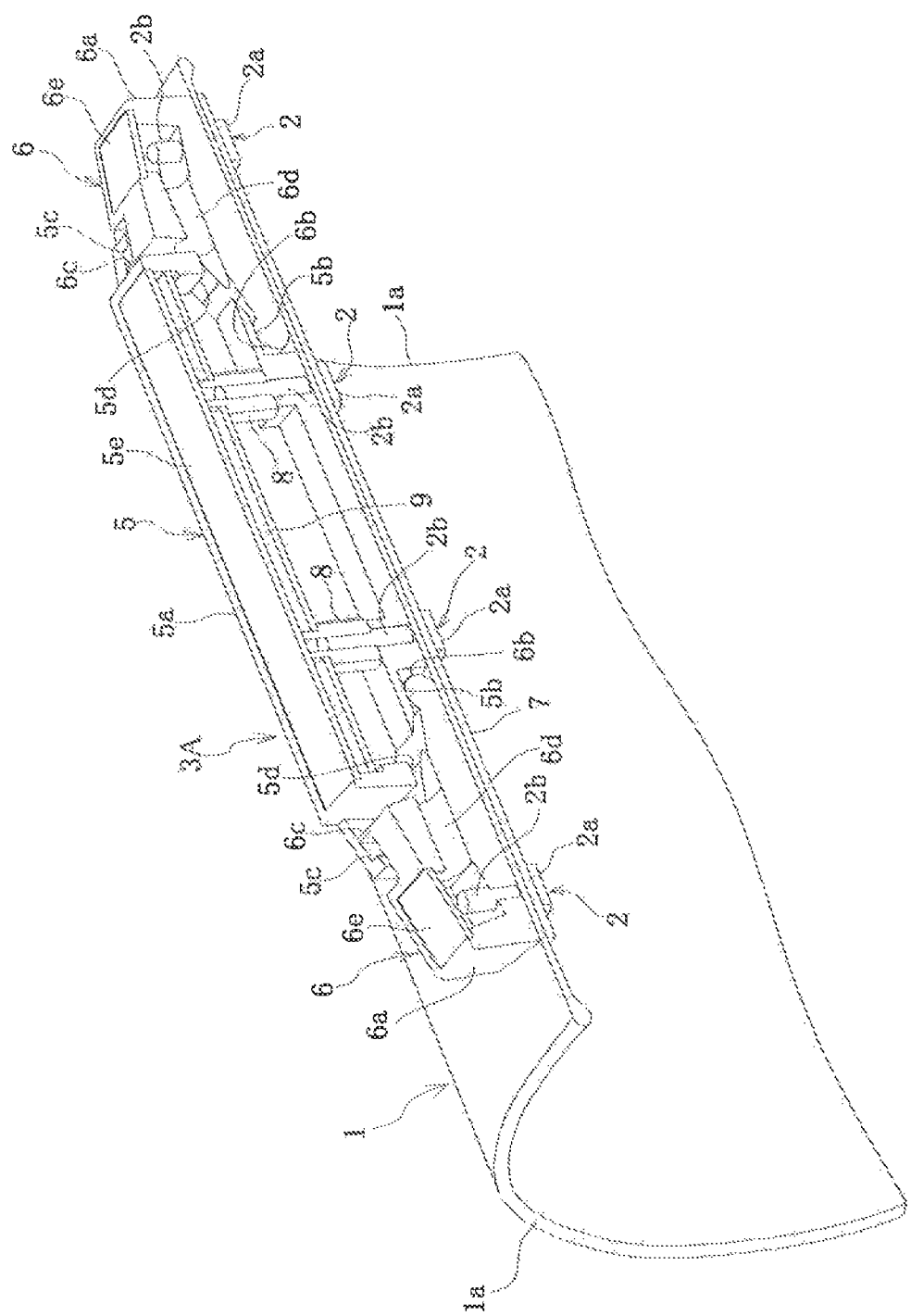

MYOELECTRIC SENSOR

CROSS-REFERENCE TO RELATED APPLICATIONS

This application is a national phase entry under 35 U.S.C. 371 of PCT international Application No. PCT/JP2016/050613 filed Jan. 12, 2016, which claims priority to Japanese Patent Application No. 2015-007661, filed Jan. 19, 2015, the disclosure of each of these applications is expressly incorporated herein by reference in their entirety.

FILED OF THE INVENTION

The present invention relates to a myoelectric sensor which is configured to be attached to a limb and detect myoelectric signals associated with a body movement.

DESCRIPTION OF THE RELATED ART

Japanese Patent Application Laid-Open Publication No. H07-163607 (patent document 1) discloses a myoelectric sensor that is attached to a limb and detects a myoelectric signal associated with a body movement. The myoelectric sensor is formed into a sheet shape and attached on a front side of a femur of a user so that a myoelectric signal indicating degree of tension of the leg is output to a controller. The controller actuates a motor for assisting the bending and stretching of the knee joint when the load of the muscles is large by analyzing the myoelectric signal together with an output signal from a pressure sensor which is attached to a sole and measuring body weight and the like and obtaining a degree of the load of the muscle during bending and stretching of the knee join.

Patent document 1: Japanese Patent Application Laid-Open Publication No. H07-163607

SUMMARY OF THE INVENTION

Task to be Solved by the Invention

In the conventional sheet-like myoelectric sensor, however, it is difficult to obtain sufficient electromyogram information because the detection range of the myoelectric signal is narrow. If the detection range of the myoelectric signal was widened, the myoelectric sensor cannot follow a deformation of the limb due to a body movement, and the myoelectric sensor would be easily peeled off.

In consideration of above-mentioned problem, the inventors have been developed a new myoelectric sensor having a plurality of myoelectric detection units arranged around the limb so as to be able to deform in accordance with the deformation of the limb due to the body movement, a new problem however arose such that a change in distance between the adjacent myoelectric detection units due to the limb deformation during the body movement or due to an attaching/detaching operation thereof may lead an excessive partial deformation and disconnection of wiring which is for transmitting information between the adjacent myoelectric detection units.

Solution for Task

The present invention advantageously solves the problem of the above-described conventional myoelectric sensor. An invented myoelectric sensor is applicable to detect myoelectric signals associated with a body movement. The myoelectric sensor has an elastically expandable and contractible annular wearing band adapted to be worn on a limb and tightly surrounding therearound, a plurality of myoelectric detection units arranged in a circumferential direction of the wearing band apart from each other and each having a plurality of myoelectric detection electrodes which is adapted to contact with a surface of the limb and to detect myoelectric signals from corresponding parts of the limb, and connecting cables which electrically connect the myoelectric detection units adjacent to each other and transmit the myoelectric signals therebetween. Each connecting cable has at least one bent portion whose bent shape changes in accordance with a change in distance between the myoelectric detection units adjacent to each other.

Effect of the Invention

According to the myoelectric sensor of the present invention, the elastically expandable and constractable annular wearing band worn around a limb can tightly surround the limb. The myoelectric detection units arranged on the wearing band spaced apart from each other in the circumferential direction of the wearing band make each myoelectric detection electrode in contact with the surface of the limb. The myoelectric detection electrodes detect myoelectric signals from the corresponding parts in the limb. The connecting cables electrically connect adjacent myoelectric detection units and transmit the detected myoelectric signals so as to output the myoelectric signals detected by the myoelectric detection units via the predetermined myoelectric detection unit. When the distance between the adjacent myoelectric detection units changes due to an expansion and contraction of the wearing band in accordance with a limb deformation caused by a body movement or an attaching/detaching operation of the wearing band to/from the limb, the bent shape of the bent portion with for example U-shape of each connecting cable having a S-shape, U-shape or bellows shape as a whole changes in accordance with the change in distance between the adjacent myoelectric detection units, so that the connecting cables are prevented from excessive partial deformation. Thus, the electrical connection can be maintained.

Therefore, according to the myoelectric sensor of the present invention, it is possible to detect the myoelectric signals over a wide range of the limb with the plurality of the myoelectric detection units and to certainly output them regardless of the limb deformation caused by the body movement or the attaching/detaching operation of the myoelectric sensor.

In the myoelectric sensor according to the present invention, it is preferable that each of the myoelectric detection units has a central part and a terminal part each having at least one myoelectric detection electrode, the central part mounting a circuit board with at least an amplifying circuit, and the terminal part being engaged with the central part movably forward and backward while being prevented from twisting with respect to the central part. According to this configuration, when the wearing band extends and contracts in its axial direction or partially in radius direction in accordance with the limb deformation due to the body movement, each of the myoelectric detection electrodes of the central part and the terminal parts locates at the same position on the surface of the limb and keeps contacting thereto, thereby the myoelectric signal at each part in the limb can be certainly detected regardless of the limb deformation caused by the body movement, and then the detected myoelectric signals can be used after amplifying with the amplifying circuit of the circuit board.

Further, in the myoelectric sensor according to the present invention, it is preferable that at least one of the plurality of myoelectric detection units has a circuit board with at least an analog-to-digital converter circuit for converting analog myoelectric signals detected by the myoelectric detection electrodes of the plurality of myoelectric detection units to digital signals and outputting them. According to this configuration, the myoelectric signals can be obtained as digital signals in which noises are hardly entered during transmitting.

Furthermore, in the myoelectric sensor of the present invention, it is preferable that at least one of the plurality of myoelectric detection units has a circuit board with at least a USB (Universal Serial Bus) controller circuit for outputting digital myoelectric signals converted with an analog-to-digital converter circuit, via a USB line. According to this configuration, the digital myoelectric signals are input into a computer via the USB line so that processing such as recording and analyzing of the myoelectric signals from a large number of the myoelectric detection units can be easily performed.

BRIEF DESCRIPTION OF THE DRAWINGS

FIG. 1 is a perspective view schematically showing an embodiment of a myoelectric sensor of the present invention.

FIG. 2 is a perspective view showing one external appearance of a plurality of myoelectric detection units in the myoelectric sensor of the above embodiment.

FIG. 3 is a perspective view showing the internal structure of the myoelectric detection unit by cutting away a part of the myoelectric detection unit.

EMBODIMENT FOR CARRYING OUT THE INVENTION

Embodiments of the present invention will be described in detail below with reference to the drawings. FIG. 1 is a perspective view schematically showing an embodiment of a myoelectric sensor according to the present invention. As shown in the figure, the myoelectric sensor of tins embodiment is provided with an elastically expandable and contractible annular wearing band 1 which is to be worn around a limb such as an arm or a leg and fitted to the limb. The myoelectric sensor is also provided with a plurality of, for example twenty, myoelectric detection units 3 which are arranged at intervals in the circumferential direction a the wearing band 1. In each of the myoelectric units 3, four myoelectric detection electrodes 2 are exposed on the inner circumferential surface of the wearing band 1 and brought into contact with the surface of the limb so that myoelectric signals are detected from the corresponding parts of the limb where the myoelectric detection electrodes 2 are in contact. The myoelectric sensor of this embodiment is further provided with connecting cables 4 which electrically connect the adjacent myoelectric detection units to each other and transmit the myoelectric signals therebetween.

Here, the wearing band 1 is knitted with stretchable fibers and has an endless annular shape. The both end portions 1a of the wearing band 1 in the axial direction are subjected to anti-loosing treatment. Further, the connecting cable 4 is made of a flat electric cable such as a flat cable or a flexible printed wiring board and loosely bent into a S shape as a whole. Therefore the bent portion 4a has a substantially U shape so that the bent shape and the bending radius thereof can change in accordance with the change of the distance between the adjacent detection units 3.

There are two types of myoelectric detection units 3: regular myoelectric detection units 3A and large myoelectric detection units 3B whose width is larger than that of the regular myoelectric detection unit 3A. In one embodiment, four large myoelectric detection units 3B are provided on the outer peripheral surface of the wearing band 1 apart from each other by approximately 90 degrees in the circumferential direction with respect to the center axis C of the wearing band 1. Between the adjacent large myoelectric detection units 3B, for example four regular myoelectric detection units 3A are arranged at substantially equal intervals and totally sixteen regular myoelectric detection units 3A are disposed on the outer circumferential surface of the wearing band 1.

FIG. 2 is a perspective view showing the appearance of the regular myoelectric detection unit 3A as one of the plurality of myoelectric detection units 3A and 3B in the myoelectric sensor of the above embodiment. FIG. 3 is a perspective view showing an internal structure of the regular myoelectric detection unit 3A by cutting one side of the regular myoelectric detection unit 3A away. Since the difference between the myoelectric detection unit 3A and the large myoelectric detection unit 3B is only an interior substrate 9 which is described later, and other than that they have a common structure to each other, the regular myoelectric detection unit 3A will be representatively explained hereafter.

The regular myoelectric detection unit 3A includes a central part 5 that is disposed so as to extend substantially along the center axis C of the wearing band 1, and terminal parts 6 adjacent to longitudinal ends of the central part 5 and engaged with the central part 5 movably forward and backward while being prevented from twisting with respect to the central part 5. The central part 5 has two myoelectric detection electrodes 2. Each of the terminal parts 6 has one myoelectric detection electrode 2 respectively.

Each of the myoelectric detection electrodes 2 is made from conductive metal and includes a head portion 2a and a shaft portion 2b which are integrally formed. The shaft portion 2b is inserted in one of through holes formed in an elastically deformable insulating resin support plate 7 at a prescribed interval. The support plates 7 are disposed on the inner peripheral surface of the wearing band 1 corresponding to the regular myoelectric detection units 3A and each of them has a length of the substantially same length as the regular myoelectric detection unit 3A. The head portion 2a is exposed at a predetermined position on the inner peripheral surface of the wearing band 1 and positioned thereto. The shaft portion 2b penetrates the wearing band 1. Each of the shaft portions 2b of two myoelectric detection electrodes 2 disposed in the central part 5 is inserted in one of through holes formed in a main body 5a of the central part 5, and then fitted or screwed into a penetration hole formed in each of conductive metal support posts 8 provided so as to correspond to the through holes of the main body 5a. The shaft portion 2b of the myoelectric detection electrode 2 disposed in each of the terminal parts 6 is fitted or screwed into a through hole formed in a main body 6a of the terminal part 6. Thus, the central part 5 and each of the terminal parts 6 are respectively fixed at predetermine positions on the outer peripheral surface of the wearing band 1. Since the two myoelectric electrodes 2 of the central part 5 are relatively close to each other, these are suitable as myoelectric detection electrodes for detecting a shallow part of the limb. On the other hand, since the myoelectric detection electrodes 2 of the two terminal parts 6 are more apart from each other than the two myoelectric electrodes 2 of the central part 5, these are suitable as myoelectric detection electrodes for detecting a deep part of the limb.

When the wearing band 1 expands and contracts in the axial direction or partially expands and contracts in the radius direction, a flat downwardly facing guide surface 5b formed at each end portion of the central part 5 slides in contact with an upwardly facing sliding portions 6b with substantially columnar shapes formed at an inner axial end of each terminal part 6. In addition, flat inwardly facing vertical wall portions 5c formed at each end portion of the central part 5 slide in contact with end surfaces of outwardly facing vertical wall portions 6c formed at the intermediate portion of each terminal part 6. Thus each of the terminal parts 6 is engaged with the central part 5 so that the terminal part 6 can move forward and backward and can pivot while being prevented from twisting with respect to the central part 5. According to this configuration, the terminal parts 6 move forward and backward and/or pivot in accordance with the expansion and contraction of the wearing band 1 in the axial direction and/or the partial expansion and contraction of the wearing band 1 in the radius direction, thereby a state in which the head portion 2a of each of the myoelectric detection electrodes 2 directs to the central axis C of the wearing band 1 is maintained by the central part 5 and each terminal part 6.

Inside the main body 5a of the central part 5, a circuit board 9 fixed and supported by the two conductive metal support posts 8 is provided. The shaft portions 2b of the two myoelectric electrodes 2 for fixing the central part 5 are electrically connected with the circuit board 9 via the support posts 8. A passage 6d is formed in the main body 6a of each terminal part 6. Openings 5d are formed at both end portions of the main body 5a of the central part 5. A wiring(s) (not shown) is(are) connected to the shaft portion 2b of the myoelectric detection electrode 2 which is fixing the terminal part 6 to the wearing band 1. The wiring(s) passes through the passage 6d and the opening 5d from the internal space of the main body 6a exposing the shaft portion 2b to the internal space of the main body 5a of the central part 5 and is(are) electrically connected to the circuit board 9.

As shown in FIG. 2, a plurality of connecting pins 5f are protruded from both side portions of the main body 5a of the central part 5. In the example shown, ten connecting pins 5f are provided at each side. An IC chip (not shown) constituting an amplifying circuit is mounted on the circuit board 9 in the main body 5a. This amplifying circuit amplifies the myoelectric signals which are coming from the two myoelectric electrodes 2 fixing the central part 5 to the wearing band 1 and the myoelectric signals which are coming from each of the myoelectric detection electrode 2 fixing the terminal part 6 to the wearing band 1, and then output to the connecting cable 4 via the connecting pins 5f at the each side portion of the main body 5a from the circuit board 9 in the regular myoelectric detection unit 3A. Connectors configured to electrically connect with the connecting pins 5f are provided at both ends of the connecting cable 4. In this way, the myoelectric signals from the four myoelectric detection electrodes 2 of each regular myoelectric detection unit 3A are collected to the large myoelectric detection unit 3B after being amplified with the amplifying circuit of the circuit board 9.

The circuit board 9 in the main body 5a of the central part 5 of each of three large myoelectric detection units 3B of the four large myoelectric detection units 3B has, in addition to the IC chip (not shown) constituting the amplifying circuit for amplifying the myoelectric signals which are coming from two myoelectric electrodes 2 fixing the central part 5 of the large myoelectric detection unit 3B to the wearing band 1 and the myoelectric signals which are coming from each myoelectric detection electrode 2 fixing the terminal part 6 of the large myoelectric detection unit 3B to the wearing band 1, an IC chip (not shown) constituting an analog-to-digital converter circuit, and a compact battery (not shown). The analog-to-digital converter circuit converts the analog myoelectric signals from for example the two regular myoelectric detection units 3A respectively locating next to each of the large myoelectric detection units 3B to the digital signal, and then output them to remaining one large myoelectric detection unit 3B. Each compact battery supplies electricity to the large myoelectric detection unit 3B and two regular myoelectric detection units 3A adjacent thereto.

The circuit hoard 9 in the main body 5a of the central part 5 of the remaining one large myoelectric detection unit 3B has, in addition to the IC chip (not shown) constituting the amplifying circuit for amplifying the myoelectric signals from two myoelectric electrodes 2 fixing the central part 5 of the large myoelectric detection unit 3B to the wearing band 1 and the myoelectric signals from each myoelectric detection electrode 2 fixing the terminal part 6 of the large myoelectric detection unit 3B to the wearing band 1, an IC chip (not shown) constituting an analog-to-digital converter circuit, an IC chip (not shown) constituting an USB controller circuit, and a compact battery (not shown). The USB controller circuit outputs the myoelectric signals from totally eighty myoelectric detection electrodes 2 of twenty myoelectric detection units 3 to an ordinary personal computer via a USB line (not shown), after converting them to the digital signals with the analog-to-digital converter circuit of each circuit board 9 of the four large myoelectric detection units 3B. The outputted myoelectric signals can be recorded in the personal computer in time-series manner and used for posteriori or real time analyses. The compact battery supplies electricity to this large myoelectric detection unit 3B and two regular myoelectric detection units 3A adjacent thereto.

A cover plate 5e is detachably and water-tightly fixed on the top of the main body 5a of each central part 5 by fitting. Similarly, a cover plate 6e is detachably and water-tightly fixed on the top of the main body 6a of each terminal part 6 by fitting. In addition, waterproof members are provided in the passage 6d of the main body 6a of each terminal part 6 and the openings 5d at the both end of the main body 5a of the central part 5 in a state in which the wiring(s) passing therethrough is(are) somewhat slackened, and thereby proving waterproofing performance to the myoelectric detection units 3.

According to the myoelectric sensor of this embodiment, the elastically expandable and contractible annular wearing band 1 worn around a limb such as an arm or a leg can closely surround the limb. The myoelectric detection units 3 including the regular myoelectric detection units 3A and the large myoelectric detection units 3B and arranged on the wearing band 1 spaced apart from each other in the circumferential direction of the wearing band 1. The myoelectric detection units 3 make the head portions 2a of the myoelectric detection electrodes 2 in contact with the surface of the limb. The myoelectric detection electrodes 2 detect myoelectric signals from the corresponding portions in the limb. The connecting cables 4 electrically connect adjacent myoelectric detection units 3 and transmit the detected myoelectric signals so as to output the myoelectric signals detected by the myoelectric detection units 3 via the predetermined large myoelectric detection unit 3B. When distances between the adjacent myoelectric detection units 3 change due to the expansion and contraction of the wearing band 1 in accordance with the limb deformation due to a body movement or an attaching/detaching operation of the wearing band 1 to/from the limb, the bent shape of the U-shape bent part of each connecting cable 4 having S-shape as a whole changes in accordance with the change of the distance between the adjacent myoelectric detection units 3, thereby preventing the connecting cable 4 from excessive partial deformation. Thus, the electrical connection can be maintained.

Therefore, according to the myoelectric sensor of this embodiment, it is possible to detect the myoelectric signals over a wide range of the limb with the plurality of the myoelectric detection units 3 and to certainly output them regardless of the limb deformation due to the body movement or the attaching/detaching operation of the myoelectric sensor.

In addition, according to the myoelectric sensor of this embodiment, each myoelectric detection unit 3 includes the central part 5 on which the circuit board 9 having at least the amplification circuit is mounted, and the terminal part 6 movably connected the central part 5 in forward and backward direction while being prevented from twisting with respect to the central part 5. Both of the central part 5 and the terminal part 6 have at least one myoelectric detection electrode 2 respectively. Thus, when the wearing band 1 extends and contracts in its axial direction or partially in radius direction in accordance with the limb deformation associated with the body movement, each of the myoelectric detection electrodes 2 of the central part 5 and the terminal parts 6 locates at the same position on the surface of the limb and keeps contacting thereto, thereby myoelectric signals of each part of the limb can be certainly detected in spite of the limb deformation caused by the body movement, and then the detected myoelectric signals can be used after amplifying with the amplifying circuit of the circuit board 9.

Furthermore, according to the myoelectric sensor of this embodiment, the circuit board 9 each provided at four of the twenty myoelectric detection units 3 also has the analog-to-digital converter circuits, and the analog-to-digital converter circuits convert the analog myoelectric signals detected by the myoelectric detection electrode 2 of the twenty myoelectric detection units 3 to the digital signals and then output. Thus, the myoelectric signal can be obtained as digital signals in which noises are hardly entered during transmitting.

Furthermore, according to the myoelectric sensor of this embodiment, the circuit board 9 provided at one of the twenty myoelectric detection units 3 also has the USB (Universal Serial Bus) controller circuit, and this USB controller circuit outputs the digital myoelectric signals converted by the analog-to-digital converter, via the USB line. Thus, the digital myoelectric signals can be input the ordinary computer via the USB line so that processing such as recording or analysis of a large number of myoelectric signals from a large number of the myoelectric detection units 3 can be performed easily.

Although the present invention has been described with reference to the illustrated examples, the present invention is not limited to the above-described examples, but can be appropriately modified within the scope of the claims. For example, in the myoelectric detection unit 3 of the myoelectric sensor of the present invention, a memory chip or memory card can be mounted on the circuit boards 9 in the main bodies 5a of several the large myoelectric detection units 3B to memorize the myoelectric signals detected with the myoelectric detection electrodes 2 after converting to the digital signals. The memorized myoelectric signals can be extracted via the USB line or directly after the measurement of the myoelectric signals.

In addition, in the myoelectric sensor of the present invention, for example, an IC chip constituting a wireless communication circuit based on a wireless LAN standard such as Wi-Fi can be mounted on the circuit board 9 in the main body 5a of the large myoelectric detection unit 3B to transmit the myoelectric signals detected by the myoelectric detection electrodes 2 to an external communication device with the wireless communication circuit, so that processing such as recording or analyzing of the transmitted myoelectric signals can be performed with a computer connected to the external communication device.

Further, in the myoelectric sensor of the present invention, the connecting cable 4 may have a flat U-shape or bellows shape as a whole instead of the flat S-shape. The connecting cable 4 may have a spiral shape to be expandable and contractible.

Furthermore, in the myoelectric sensor of the present invention, for example the radius of the wearing band 1, the number of the regular myoelectric detection unit 3A and the large myoelectric detection unit 3B constituting the myoelectric detection unit 3, and the number of the myoelectric detection electrodes 2 of each myoelectric detection unit 3 can be appropriately changed according to the necessity, such as the radius of the limb. The myoelectric detection units 3 may be constituted by either the regular myoelectric 3A detection units or the large myoelectric detection units 3B.

INDUSTRIAL APPLICABILITY

According to the myoelectric sensor of the present invention, it is possible to detect the myoelectric signals over a wide range of the limb with the plurality of the myoelectric detection units and to certainly output them despite the limb deformation caused by the body movement or the attaching/detaching operation of the myoelectric sensor.

EXPLANATION SIGN

1 Wearing band
2 Myoelectric detection electrode
2a Head
2b Shaft
3 Myoelectric detection unit
3A Regular myoelectric detection unit
3B Large myoelectric detection unit
4 Connecting cable
4a Bent portion
5 Central part
5a Main body
5b Downwardly facing guide portion
5c Inwardly facing vertical wall
5d Opening
5e Cover plate
5f Connecting pin
6 Terminal part
6a Main body
6b Upwardly facing sliding portion
6c Outwardly facing vertical wall portion 6*d* Passage
6*e* Cover plate
7 Support plate
8 Support post
9 Circuit board

The invention claimed is:

1. A myoelectric sensor for detecting myoelectric signals caused by a body movement comprising:
   an elastically expandable and contractible annular wearing band adapted to be worn on a limb and tightly surrounding therearound;
   a plurality of myoelectric detection units arranged in a circumferential direction of said wearing band apart from each other and each having a plurality of myoelectric detection electrodes which adapts to contact with a surface of the limb and to detect myoelectric signals from corresponding parts of the limb; and
   connecting cables which electrically connect said myoelectric detection units adjacent to each other and transmit the myoelectric signals therebetween,
   wherein each of said connecting cables has at least one bent portion whose bent shape changes in accordance with a change in distance between the myoelectric detection units adjacent to each other,
   wherein each of said plurality of myoelectric detection units comprises a central part and a terminal part each having at least one of the myoelectric detection electrodes, the central part of at least one of the plurality of myoelectric detection units mounting a circuit board with at least an amplifying circuit, and the terminal part being engaged with said central part movably forward and backward while being prevented from twisting with respect to said central part.

2. The myoelectric sensor according to claim 1, wherein at least one of the connecting cables has an S-shape as a whole.

3. The myoelectric sensor according to claim 1, wherein the circuit board has at least an analog-to-digital converter circuit for converting analog myoelectric signals detected by said myoelectric detection electrodes of said plurality of myoelectric detection units to digital signals and outputting them.

4. The myoelectric sensor according to claim 1, wherein the circuit board has at least a USB controller circuit for outputting digital myoelectric signals converted with an analog-to-digital converter circuit, via a USB line.

\* \* \* \* \*